United States Patent
Vancurova et al.

(10) Patent No.: US 9,993,489 B2
(45) Date of Patent: Jun. 12, 2018

(54) METHODS FOR TREATING SOLID TUMOR CANCERS USING A HISTONE DEACETYLASE INHIBITOR AND AN IκB KINASE INHIBITOR

(71) Applicant: St. John's University, Queens, NY (US)

(72) Inventors: Ivana Vancurova, New Hyde Park, NY (US); Himavanth R. Gatla, Queens, NY (US); Bipradeb Singha, Philadelphia, PA (US)

(73) Assignee: St. John's University, Queens, NY (US)

( * ) Notice: Subject to any disclaimer, the term of this patent is extended or adjusted under 35 U.S.C. 154(b) by 0 days. days.

(21) Appl. No.: 15/411,023

(22) Filed: Jan. 20, 2017

(65) Prior Publication Data

US 2017/0209467 A1    Jul. 27, 2017

Related U.S. Application Data

(60) Provisional application No. 62/281,276, filed on Jan. 21, 2016.

(51) Int. Cl.
| | |
|---|---|
| *A61K 31/616* | (2006.01) |
| *A61K 31/167* | (2006.01) |
| *A61K 31/395* | (2006.01) |
| *A61K 31/277* | (2006.01) |
| *A61K 9/00* | (2006.01) |

(52) U.S. Cl.
CPC .......... *A61K 31/616* (2013.01); *A61K 9/0019* (2013.01); *A61K 31/167* (2013.01); *A61K 31/277* (2013.01); *A61K 31/395* (2013.01)

(58) Field of Classification Search
CPC .. A61K 31/616; A61K 9/0019; A61K 31/167; A61K 31/277; A61K 31/395

USPC .......................................................... 514/161
See application file for complete search history.

(56) References Cited

PUBLICATIONS

Dai et al., "Disruption of IκB Kinase (IKK)-mediated RelA Serine 536 Phosphorylation Sensitizes Human Multiple Myeloma Cells to Histone Deacetylase (HDAC) Inhibitors," J. Biol. Chem., vol. 286, No. 39, pp. 34036-34050 (2011).
Khabele, "The therapeutic potential of class I selective histone deacetylase inhibitors in ovarian cancer," Frontiers in Oncology, vol. 4, No. 111, pp. 1-8 (2014).
Vancurova et al., "Regulation and function of nuclear IκBα in inflammation and cancer," Am. J. Clin. Exp. Immunol., vol. 1, No. 1, pp. 56-66 (2012).
Deng et al., "The Novel IKK2 Inhibitor LY2409881 Potently Synergizes with Histone Deacetylase Inhibitors in Preclinical Models of Lymphoma through the Downregulation of NF-κB," Clin. Cancer Res., vol. 21, No. 1, pp. 134-145 (2015).
Singha et al., "Quantitative analysis of bortezomib-induced IL-8 gene expression in ovarian cancer cells," Methods Mol. Biol., vol. 1172, pp. 295-304 (2014).
"IKK inhibitors NFκB Signalling: Tocris Bioscience," http://www.tocris.com/newsletter/IKK_web-alert.html (last visited Jul. 6, 2017).

*Primary Examiner* — Yevgeny Valenrod
(74) *Attorney, Agent, or Firm* — Fitzpatrick, Cella, Harper & Scinto (57) ABSTRACT

Methods for the treatment of solid tumor cancers, specifically ovarian cancer and drug-resistant solid tumors, are disclosed. A method comprises administering a combination therapy including a therapeutically effective amount of an HDAC inhibitor and a therapeutically effective amount of an IKK inhibitor to a subject in need thereof. Pharmaceutical compositions and kits comprising an HDAC inhibitor and an IKK inhibitor are also disclosed.

17 Claims, 6 Drawing Sheets

Representative image of tumor growth:

Figure 7B

Tumors after excision:

METHODS FOR TREATING SOLID TUMOR CANCERS USING A HISTONE DEACETYLASE INHIBITOR AND AN IκB KINASE INHIBITOR

This application claims the benefit of U.S. Provisional Application No. 62/281,276 filed on Jan. 21, 2016, the entire disclosure of which is incorporated by reference herein.

FIELD OF THE INVENTION

The present invention discloses a method for treating a solid tumor cancer comprising administering to a subject in need thereof a therapeutically effective amount of a histone deacetylase (HDAC) inhibitor and a therapeutically effective amount of an IκB kinase (IKK) inhibitor. Also disclosed are pharmaceutical compositions, kits, and methods of determining a susceptibility of a cancer to a combination therapy comprising an HDAC inhibitor and an IKK inhibitor.

BACKGROUND OF THE INVENTION

Ovarian cancer is the most lethal of the gynecological cancers. Ovarian cancer is diagnosed annually in nearly a quarter of a million women globally, and is responsible for 140,000 deaths each year. In the U.S., 21,980 new cases and 14,270 deaths were estimated in 2014. Khabele, D., "The therapeutic potential of class I selective histone deacetylase inhibitors in ovarian cancer," Frontiers in Oncology, Vol. 4, pp. 1-8, 1 (2014). Current treatment for ovarian cancer entails a combination of cytoreductive surgery and platinum-based chemotherapy. Id. Despite even the best initial results, most ovarian cancers relapse with recurrent tumors and options for treatment of recurrent disease are restricted by few effective drugs and frequent dose-limiting toxicities of traditional drugs. Id. New approaches are urgently needed that can extend the disease-free interval, re-sensitize tumors to platinum-based drugs, and minimize toxic effects.

Histone deacetylases (HDACs) are a family of enzymes that regulate gene expression by removing acetyl groups from lysine residues on histones and non-histone proteins. Inhibition of HDACs with small molecules has led to the development of HDAC inhibitors, primarily for use in hematologic malignancies. HDAC inhibitors are a structurally diverse set of chemical compounds traditionally classified into four major categories: hydroxamic acids (e.g., vorinostat); benzamides (e.g., MS-275); short aliphatic acids (e.g., valproic acid, VPA); and cyclic peptides (e.g., romidepsin or depsipeptide). Id. HDAC inhibitors increase acetylation of histones and other non-histone proteins, resulting in changes in gene expression, induction of apoptosis, and inhibition of angiogenesis and metastasis. They are effective for use in cancer treatment because of their ability to differentiate between normal cells and cancer cells at therapeutic dosages. HDAC inhibitors, for example, vorinostat (SAHA, ZOLINZA®) and romidepsin (FK228, ISTODAX®), are known to be effective in treating hematological malignancies. In fact, vorinostat and romidepsin are FDA-approved for the treatment of cutaneous and peripheral T-cell lymphoma. However, clinical trials with an HDAC inhibitor as a single agent in the treatment of solid tumors, including ovarian cancer, have produced poor results. Khabele, Abstract.

Nuclear factor-kappa B (NF-κB) is a transcription factor that comprises five different proteins and is found in all cell types. It is involved in cellular responses to stimuli, such as cytokines and stress, and plays a key role in regulating the immune response to infection and inflammation. http://www.tocris.com/newsletter/IKK_web-alert.html. In unstimulated cells, NF-κB dimers are sequestered in the cytoplasm in an inactive complex with inhibitory protein, called inhibitor of kappa B (IκB). IκB inactivates NF-κB by masking the nuclear localization signals (NLS), and preventing translocation of NF-κB proteins to the nucleus.

Activation of NF-κB occurs via degradation of IκB, a process that is initiated by IκB phosphorylation by IκB kinase (IKK). Phosphorylated IκB is then ubiquitinated and degraded by the proteasome. Once IκB is degraded, NF-κB translocates to the nucleus and induces transcription of NF-κB-dependent genes. In addition to phosphorylating IκB, resulting in its proteasomal degradation, IKK can also directly phosphorylate the p65 subunit of NF-κB, resulting in its transcriptional activation. Vancurova, I, et al., "Regulation and function of nuclear IκBα in inflammation and cancer," Am. J. Clin. Exp. Immunol., Vol. 1, No. 1, pp. 56-66 (2012).

NF-κB regulates the genes involved in inflammation, cell proliferation, and cell survival, and NF-κB activity is constitutively increased in many human tumors. Constitutive activation of NF-κB can result from a mutation in NF-κB itself or in genes that control its activity, e.g., IκB. Specifically, constitutive activation of NF-κB is observed in a number of lymphoma subtypes. Deng, C., et al., "The Novel IKK2 Inhibitor LY2409881 Potently Synergizes with Histone Deacetylase Inhibitors in Preclinical Models of Lymphoma through the Downregulation of NF-κB," Clin. Cancer Res., Vol. 21, No. 1, pp. 134-145 (2015). One of the genes that is regulated by NF-κB is the pro-inflammatory and pro-angiogenic chemokine interleukin-8 (IL-8) that induces tumor cell survival, proliferation, angiogenesis, and metastasis. IL-8 production is increased in many types of cancer, and correlates with cancer progression and poor prognosis. Blocking IKK and NF-κB activation can stop tumor cell proliferation and induce cell death. Therefore, IKK inhibitors have been identified for use in the treatment of cancers.

IKK inhibitors have been used in combination with HDAC inhibitors in the treatment of hematological malignancies, such as lymphoma and leukemia, but not for the treatment of solid tumor cancers because each has shown disappointing results as a single agent in the treatment of solid tumor cancers, such as ovarian cancer and drug-resistant tumors.

SUMMARY OF THE INVENTION

The present disclosure provides a method for treating a solid tumor cancer comprising administering to a subject in need thereof a therapeutically effective amount of a histone deacetylase (HDAC) inhibitor and a therapeutically effective amount of an IκB kinase (IKK) inhibitor. The HDAC inhibitor and IKK inhibitor may be administered in combination, sequentially or concomitantly.

Also disclosed is a method for determining a susceptibility of a cancer to treatment with a combination therapy comprising an HDAC inhibitor and an IKK inhibitor, comprising the steps of: isolating cancer or neoplastic cells or cell lines; treating the isolated cancer or neoplastic cells or cell lines with the combination therapy; and assessing the effect of the treatment on IL-8 production and cell survival.

Other embodiments are a pharmaceutical composition comprising: an HDAC inhibitor; an IKK inhibitor; and at least one pharmaceutically acceptable excipient, and a kit comprising: an HDAC inhibitor; and an IKK inhibitor.

DETAILED DESCRIPTION OF THE INVENTION

I. Methods of Use

The present disclosure provides a novel method for treating a solid tumor cancer. That method includes administering to a subject in need thereof a therapeutically effective amount of a histone deacetylase (HDAC) inhibitor and a therapeutically effective amount of an IκB kinase (IKK) inhibitor.

Any HDAC inhibitor known for use in the art may be used in the present disclosure, as well as any combination thereof. In an embodiment, the HDAC inhibitor is vorinostat (SAHA, ZOLINZA®), romidepsin (FK228, ISTODAX®), or a combination thereof. In one embodiment, the HDAC inhibitor is vorinostat, and in another, the HDAC inhibitor is romidepsin.

Any IKK inhibitor known for use in the art may be used in the present disclosure, as well as any combination thereof. In an embodiment, the IKK inhibitor is Bay-117085, Bay-117082, PS-1145, SC-514, SPC-839, MLN120B, IMD-0354, BMS-345541, aspirin or any combination thereof. In another embodiment, the IKK inhibitor is Bay-117085.

In an embodiment, the method comprises administering an HDAC inhibitor selected from the group consisting of vorinostat (SAHA, ZOLINZA®), romidepsin (FK228, ISTODAX®), and any combination thereof, and an IKK inhibitor selected from the group consisting of Bay-117085, Bay-117082, PS-1145, SC-514, SPC-839, MLN120B, IMD-0354, BMS-345541, aspirin, and any combination thereof. In another embodiment, the HDAC inhibitor is vorinostat or romidepsin, and the IKK inhibitor is Bay-117085.

Examples of solid tumors according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. The invention is applicable to sarcomas and epithelial cancers, such as ovarian cancers and breast cancers. In a certain embodiment, the solid tumor cancer is a bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, or any combination thereof.

In another embodiment, the solid tumor is a member of the group consisting of lung cancer, bone cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the sexual or reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the bladder, cancer of the kidney, renal cell carcinoma, neoplasms of the central nervous system (CNS), neuroectodermal cancer, spinal axis tumors, glioma, meningioma, and pituitary adenoma.

In an embodiment, the solid tumor cancer is ovarian cancer, prostate cancer, breast cancer, cervical cancer, or any combination thereof. In a certain embodiment, the solid tumor cancer is ovarian cancer or another drug-resistant solid tumor. In another embodiment, the solid tumor cancer is ovarian cancer. In another embodiment, the solid tumor cancer is prostate cancer, preferably, androgen-independent prostate cancer. In another embodiment, the solid tumor cancer is breast cancer, preferably, triple-negative breast cancer. In another embodiment, the solid tumor cancer is cervical cancer.

The term "drug-resistant" or "drug-resistance" refers to the condition when a disease has a reduced response or does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In an embodiment, drug-resistance is intrinsic. In another embodiment, the drug-resistance is acquired. As used herein, the term "drug-resistance" is meant to include, but is not limited to, HDAC inhibitor resistance (e.g., vorinostat or romidepsin resistance), platinum drug resistance, taxane resistance, steroid resistance, anthracycline resistance, imatinib-resistance, dasatinib-resistance, and/or nilotinib-resistance.

As used herein, "subject in need thereof" is a subject with a cancerous solid tumor in need of treatment for at least one tumor.

The "subject," as used herein, is an animal. In one embodiment, the subject is a mammal. In another embodiment, the subject is a human.

The HDAC inhibitor may be administered in combination, sequentially, or concomitantly with the IKK inhibitor. In one embodiment, the HDAC inhibitor is administered in combination with the IKK inhibitor. In another embodiment, the HDAC inhibitor is administered sequentially with the IKK inhibitor. In a further embodiment, the HDAC inhibitor is administered concomitantly with the IKK inhibitor.

"In combination with" and "combination therapy" refer, in certain embodiments, to the concurrent administration to a patient of an HDAC inhibitor and an IKK inhibitor. When administered in combination, an HDAC inhibitor and an IKK inhibitor can be administered at the same time or sequentially in any order at different points in time. Thus, an HDAC inhibitor and an IKK inhibitor can be administered separately but sufficiently closely in time so as to provide the desired therapeutic effect. In general, in a combination therapy of the present disclosure, a therapeutically effective amount of each of an HDAC inhibitor and an IKK inhibitor may be administered sequentially, i.e., serially, or a therapeutically effective amount of both of the HDAC inhibitor and IKK inhibitor may be administered together.

"Concomitant administration" of an HDAC inhibitor and an IKK inhibitor means administration of an HDAC inhibitor and an IKK inhibitor at such time that both will have a therapeutic effect. Such concomitant administration may involve concurrent (i.e., at the same time), prior, or subsequent administration of one active ingredient (i.e., the HDAC inhibitor or IKK inhibitor) with respect to the administration of the other active ingredient. When administered separately, administration of the HDAC inhibitor and the IKK inhibitor may be separated by one to twenty-four hours, one day, two days, three days, four days, five days, one week, two weeks, or more, and preferably, separated by about six hours to about twenty-four hours.

When administered sequentially, the HDAC inhibitor and the IKK inhibitor are administered in two or more administrations.

When administered concurrently, the HDAC inhibitor and the IKK inhibitor are administered at the same time, either together in one pharmaceutical formulation or as separate formulations.

As used herein, "therapeutically effective amount" refers to an amount of the HDAC inhibitor or IKK inhibitor, which is effective in combination with the other active ingredient, upon single or multiple dose administration (e.g., bolus and/or maintenance doses) to a subject, in inhibiting, delaying or reducing the growth of a solid tumor. Therapeutically effective is also intended to refer to an amount of the HDAC inhibitor or IKK inhibitor (when used in combination with the other active) suitable for diagnostic uses. Thus, a therapeutically effective amount of an HDAC inhibitor is the amount of the HDAC inhibitor that is needed to treat a solid tumor cancer in combination with an IKK inhibitor. Likewise, a therapeutically effective amount of an IKK inhibitor is the amount of the IKK inhibitor that is needed to treat a solid tumor cancer in combination with an HDAC inhibitor.

In one embodiment of the invention, a therapeutically effective amount of the HDAC inhibitor and/or the IKK inhibitor may be administered by subcutaneous, intramuscular, or intravenous route of administration. For example, it may be administered intravenously as a sterile solution. In another embodiment, a therapeutically effective amount of the HDAC inhibitor and/or the IKK inhibitor is administered by oral, nasal, or pulmonary route, or to a mucosal region (mouth, rectum, or vagina). In a preferred embodiment thereof, the HDAC inhibitor and/or the IKK inhibitor is administered intravenously, intra-articularly or orally.

The HDAC inhibitor and IKK inhibitor used in accordance with this disclosure may be provided in any form known in the art. Pharmaceutically acceptable forms may be preferred. The therapeutically effective amount of the HDAC inhibitor and IKK inhibitor will vary depending on the patient, the cancer or neoplasm being treated, stage of the cancer, pathology of the cancer or neoplasm, genotype of the cancer or neoplasm, phenotype of the cancer or neoplasm, the route of administration, etc. In addition, as will be appreciated by one of ordinary skill in the art, the therapeutically effective amount of the HDAC inhibitor and IKK inhibitor may vary depending on the form of the active ingredient being administered. The dosages given herein are dose equivalents with respect to the active ingredient.

The therapeutically effective amount of the HDAC inhibitor when used in combination with the IKK inhibitor in accordance with the invention will typically range from about 0.001 mg/kg to about 1 g/kg of body weight per day; in another embodiment, from about 0.01 mg/kg to about 600 mg/kg body weight per day; in another embodiment, from about 0.01 mg/kg to about 250 mg/kg body weight per day; in another embodiment, from about 0.01 mg/kg to about 400 mg/kg body weight per day; in another embodiment, from about 0.01 mg/kg to about 200 mg/kg of body weight per day; in another embodiment, from about 0.01 mg/kg to about 100 mg/kg of body weight per day; in one embodiment, from about 0.01 mg/kg to about 25 mg/kg body weight per day; in another embodiment, from about 0.1 mg/kg to about 10 mg/kg body weight per day; in another embodiment, from about 0.001 mg/kg to about 100 mg/kg of body weight per day; in another embodiment, from about 0.001 mg/kg to about 10 mg/kg of body weight per day; and in another embodiment, from about 0.001 mg/kg to about 1 mg/kg of body weight per day.

In a certain embodiment, the therapeutically effective amount of the HDAC inhibitor when used in combination with the IKK inhibitor in accordance with the invention is about 0.001 mg/kg to about 1 g/kg of body weight per day and the HDAC inhibitor is administered intravenously, intra-articularly or orally. Preferably, the HDAC inhibitor may be administered intravenously or orally.

The HDAC inhibitor may be administered intravenously over a period of about 30 minutes to about 10 hours, preferably, from about 1 hour to about 8 hours, more preferably, over a period of about 2 hours to about 6 hours, and still more preferably, over a period of about 4 hours. The amount of HDAC inhibitor administered intravenously may be about 5 mg/m$^2$ to about 20 mg/m$^2$, preferably about 8 mg/m$^2$ to about 15 mg/m$^2$, more preferably about 10 mg/m$^2$ to about 14 mg/m$^2$, and still more preferably about 14 mg/m$^2$. The amount in each dosing, as well as the frequency of administration, may be consistent over a 28-day cycle or over the course of treatment, or it may vary between doses. The HDAC inhibitor may be administered intravenously once daily for 1 to 7 days each week (consecutive or otherwise), or once per week, once per two weeks, once per three weeks or once monthly. In an embodiment, the HDAC inhibitor may be administered intravenously for about 4 hours, at about 14 mg/m² on days 1, 8, and 15 of a 28-day cycle.

The HDAC inhibitor may be administered orally in a dosage of about 100 mg to about 800 mg, preferably about 100 mg to about 600 mg, more preferably, about 200 mg to about 600 mg, and still more preferably, about 300 mg to about 400 mg. The HDAC inhibitor may be administered orally once daily, twice daily, or three time daily. It may be administered for 1 to 7 days each week (consecutive or spaced out. e.g., every other day, every third, fourth, fifth, or sixth day), or once per week, once per two weeks, once per three weeks or once monthly. In an embodiment, the HDAC inhibitor may be administered orally in a dosage of about 300 mg to about 400 mg once daily for 5 consecutive days each week. The cycle may be repeated every 28 days. In certain embodiments, the 28-day cycle is repeated more than 10 times, preferably, 2-20 times, more preferably, 3-10 times. In another certain embodiment, the cycle repeats as long as the patient is responding. The amount in each dosing, as well as the frequency of administration, may be consistent over a 28-day cycle or over the course of treatment, or it may vary between doses.

The therapeutically effective amount of the IKK inhibitor when used in combination with the HDAC inhibitor in accordance with the invention will typically range from about 0.001 mg/kg to about 1 g/kg of body weight per day; in another embodiment, from about 0.01 mg/kg to about 600 mg/kg body weight per day; in another embodiment, from about 0.01 mg/kg to about 250 mg/kg body weight per day; in another embodiment, from about 0.01 mg/kg to about 400 mg/kg body weight per day; in another embodiment, from about 0.01 mg/kg to about 200 mg/kg of body weight per day; in another embodiment, from about 0.01 mg/kg to about 100 mg/kg of body weight per day; in one embodiment, from about 0.01 mg/kg to about 25 mg/kg body weight per day; in another embodiment, from about 0.1 mg/kg to about 10 mg/kg body weight per day; in another embodiment, from about 0.001 mg/kg to about 100 mg/kg of body weight per day; in another embodiment, from about 0.001 mg/kg to about 10 mg/kg of body weight per day; and in another embodiment, from about 0.001 mg/kg to about 1 mg/kg of body weight per day.

In a certain embodiment, the therapeutically effective amount of the IKK inhibitor when used in combination with the HDAC inhibitor in accordance with the invention is about 0.001 mg/kg to about 1 g/kg of body weight per day and the IKK inhibitor is administered intravenously, intra-articularly or orally. Preferably, the IKK inhibitor may be administered intravenously or orally.

The IKK inhibitor may be administered intravenously over a period of about 30 minutes to about 10 hours, preferably about 1 hour to about 8 hours, more preferably about 2 hours to about 6 hours, and more preferably, about 4 hours. The amount of IKK inhibitor administered intravenously may be about 5 mg/m² to about 20 mg/m², preferably about 8 mg/m² to about 15 mg/m², more preferably about 10 mg/m² to about 14 mg/m², and still more preferably about 14 mg/m². The amount in each dosing, as well as the frequency of administration, may be consistent over a 28-day cycle or over the course of treatment, or it may vary between doses. The IKK inhibitor may be administered intravenously once daily for 1 to 7 days each week (consecutive or otherwise), or once per week, once per two weeks, once per three weeks or once monthly. In an embodiment, the IKK inhibitor may be administered intravenously for about 4 hours, at about 14 mg/m² on days 1, 8, and 15 of a 28-day cycle. The cycle may be repeated every 28 days. In certain embodiments, the 28-day cycle is repeated more than 10 times, preferably, 2-20 times, more preferably, 3-10 times. In another certain embodiment, the cycle repeats as long as the patient is responding.

The IKK inhibitor may be administered orally in a dosage of about 100 mg to about 2000 mg, preferably about 200 mg to about 1000 mg, more preferably, about 200 mg to about 600 mg, and still more preferably, about 300 mg to about 500 mg. The IKK inhibitor may be administered orally once daily, twice daily, three times daily or four times daily. It may be administered for 1 to 7 days each week (consecutive or otherwise), once per week, once per two weeks, once per three weeks or once monthly. The cycle may be repeated every 28 days. In certain embodiments, the 28-day cycle is repeated more than 10 times, preferably, 2-20 times, more preferably, 3-10 times. In another certain embodiment, the cycle repeats as long as the patient is responding. The amount in each dosing, as well as the frequency of administration, may be consistent over a 28-day cycle or over the course of treatment, or it may vary between doses.

The IKK inhibitor and HDAC inhibitor may be administered in the same dosing schedule or one active may be administered more frequently than the other active. The IKK inhibitor may be administered more frequently than the HDAC inhibitor, or the HDAC inhibitor may be administered more frequently than the IKK inhibitor. In an embodiment, the HDAC inhibitor is administered intravenously and the IKK is administered orally, and the IKK inhibitor is administered more frequently than the HDAC inhibitor.

In an embodiment, both the HDAC and IKK inhibitor are administered orally. The HDAC inhibitor and the IKK inhibitor may be administered orally in combination, sequentially, or concomitantly. The doses may be administered at the same time or at different times, preferably, in combination at the same time. When administered sequentially, the oral administration of the HDAC inhibitor and the IKK inhibitor may be separated by one to twenty-four hours, one day, two days, three days, four days, five days, one week, two weeks, or more, and preferably, separated by about six hours to about twenty-four hours.

In another embodiment, the HDAC inhibitor is be administered orally, while the IKK inhibitor is administered via a different route, preferably intravenously. In an embodiment thereof, the HDAC inhibitor is vorinostat and is administered orally, while the IKK inhibitor is administered intravenously. In yet another embodiment, the IKK inhibitor is administered orally, while the HDAC inhibitor is administered via a different route, preferably intravenously. In an embodiment thereof, the HDAC inhibitor is romidepsin and is administered intravenously, while the IKK inhibitor is administered orally.

Progression of ovarian cancer is associated with the increased expression of the pro-inflammatory chemokine interleukin-8 (IL-8), which is a pro-inflammatory and pro-angiogenic chemokine that induces tumor cell survival, proliferation, angiogenesis and metastasis. IL-8 production is increased in metastatic ovarian cancer cells, and other solid tumors, and correlates with cancer progression and poor prognosis. The inventors found that HDAC inhibitors, for example, vorinostat and romidepsin, unexpectedly increase the IL-8 production in cancer cells, for example, ovarian and cervical cancer cells in vitro. Since IL-8 promotes survival of ovarian cancer cells, these results indicate that the HDAC inhibitor-induced IL-8 production may be responsible for the limited effectiveness of HDAC inhibitors as single agents in ovarian cancer treatment. Importantly, it has been discovered herein that anti-inflammatory drugs, such as Bay-117085 and aspirin, which inhibit IKK activity, decrease the HDAC inhibitor-induced IL-8 production in ovarian and cervical cancer cells in vitro. IKK inhibition increases the HDAC inhibitor effectiveness in vivo.

The inhibition of IKK activity decreases the HDAC inhibitor-induced IL-8 production. The effect is particularly pronounced in highly metastatic ovarian cancer cells, but can be observed also in other cancer cells. Importantly, it has been discovered herein that the combination of an HDAC inhibitor and an IKK inhibitor substantially reduces ovarian tumor growth in vivo when compared to either drug alone. In one embodiment, the combination of an HDAC inhibitor and an IKK inhibitor, such as Bay-117085, Bay-117082, PS-1145, SC-514, SPC-839, MLN120B, IMD-0354, BMS-345541, aspirin or any combination thereof, substantially reduces the ovarian tumor growth in vivo in nude mice implanted with ovarian cancer xenografts, when compared to either drug alone.

In sum, an HDAC inhibitor increases IL-8 production in solid tumor cancer cells, such as ovarian and cervical cancer cells, and an IKK inhibitor suppresses the HDAC inhibitor-induced IL-8 production. According to the present disclosure, the inventors surprisingly found that when an HDAC inhibitor and an IKK inhibitor are administered together, the combination therapy reduces the IL-8 production and tumor growth compared to either drug alone.

Another embodiment is directed to a method for determining a susceptibility of a cancer to a treatment with a combination therapy comprising a HDAC inhibitor and an IKK inhibitor, comprising the steps of: isolating cancer or neoplastic cells or cell lines; treating the isolated cancer or neoplastic cells or cell lines with the combination therapy; and assessing the effect of the treatment on IL-8 production and cell survival of the cancer or neoplastic cells or cell lines. Such a method may be used for clinical purposes with in vitro testing.

Any cancer or neoplastic cells or cell lines may be used in this method. The cells may be at any stage of differentiation or development. In one embodiment, the cells are animal cells, preferably, mammalian cells, and more preferably human cells. In certain embodiments, the cells may be derived from a male or a female human in any stage of development.

Another embodiment uses cancer or neoplastic cells derived from a genetically engineered animal, such as a transgenic or knockout mouse. The cancer or neoplastic cells used may be wild type or mutant cells, or normal cells. When they are cancer cells, they may be derived from a solid tumor. For example, the cells may be derived from a human patient's tumor from a biopsy or surgical excision. The cancer cells may alternatively be derived from a blood sample or from a bone marrow biopsy. In an embodiment, the cancer cells are derived from a lymph node biopsy.

In yet another embodiment, the cells used in the method may be derived from cancer cell lines representing any histological and molecular subtypes. For example, the cells may be wild type, mutated, or transfected with different vectors or plasmids. In a certain embodiment, the cell lines are resistant to one of the active ingredients. In an embodiment, the cell line is resistant to an HDAC inhibitor.

Isolating the cancer or neoplastic cells or cell lines in accordance with this disclosure may be accomplished using any method known in the art.

The isolated cells or cell lines are treated by incubating the cells with an HDAC inhibitor and an IKK inhibitor, as defined in the embodiments above. The in vitro concentration of each active may be from 0.1 nM to 10 mM. The incubation time with the HDAC inhibitor and IKK inhibitor may be concurrent or sequential, preferably concurrent, and may be from 3 to 96 hours.

Assessing the effect of the treatment on IL-8 production and cell survival is be performed in accordance with any known method in the art. Cell survival refers to the viability of the cancer or neoplastic cells or cell lines. Treatment with the combination therapy in accordance with the disclosure should reduce the viability of the cancer or neoplastic cells or cell lines.

The method of the invention may be useful in determining whether a patient will positively respond to the combination therapy, and/or in determining the dosage needed to treat a cancerous tumor. This method, by determining the susceptibility of a cancer to the combination therapy, may prevent unnecessary administration of medicine/active ingredients that will have no positive effect to a patient. The results of the method may indicate that a lower dose of one or both of the active ingredients is needed thereby reducing costs, waste and negative side effects to the patient by eliminating the unnecessary administration of a higher dose.

The cells or cell lines treated with the combination therapy may be used to assay numerous and various pro-inflammatory markers. For example, mRNA expression and protein release of the pro-inflammatory and pro-angiogenic chemokine interleukin-8 (IL-8) may be measured.

The method may further comprise the step of determining the therapeutically effective amount of the combination therapy, preferably for each of the HDAC inhibitor and the IKK inhibitor. The therapeutically effective amount of in vitro concentrations of the HDAC and IKK inhibitors, and the incubation times will vary depending on the cells or cell lines that are used.

In one embodiment, the assessed IL-8 production and cell survival of the cells treated with the combination therapy are compared to the same isolated cancer or neoplastic cells or cell lines that have been treated with an HDAC inhibitor alone. While an HDAC inhibitor alone induces the IL-8 mRNA and protein expression, the combination therapy of an HDAC and an IKK inhibitor inhibits HDAC inhibitor-induced IL-8 production. Since IL-8 promotes cancer cell survival and proliferation, the combination of the HDAC and the IKK will reduce cancer cell survival and proliferation, and slow down tumor growth.

II. Pharmaceutical Compositions

Another embodiment of the invention is directed to a pharmaceutical composition comprising: a histone deacetylase (HDAC) inhibitor; and an IκB kinase (IKK) inhibitor.

In a certain embodiment, the pharmaceutical composition is administered to a subject in need thereof for use in the treatment of a solid tumor cancer.

The pharmaceutical composition may further contain a pharmaceutically acceptable carrier or excipient. The term "pharmaceutically acceptable" means a nontoxic material that is compatible with the physical and chemical characteristics of the HDAC inhibitor and IKK inhibitor (each referred to as "the active" or "active ingredient," and together "active ingredients") and does not interfere with the effectiveness of the biological activity of the active ingredients. The compositions may contain various diluents, fillers, salts, buffers, stabilizers, solubilizers, and other materials well known in the art. The characteristics of the carrier will depend on the route of administration, and are generally well known in the art.

The pharmaceutical composition may be adapted for enteral administration—administration of the composition, wherein the composition is absorbed through the digestive tract, e.g., oral ingestion, rectal administration. In other embodiments, the pharmaceutical composition of the invention may be adapted for parenteral administration—administration of the composition, wherein the composition is introduced via a route other than digestive tract, e.g., intravenous, intra-articular, subcutaneous, cutaneous, nasal, pulmonary, vaginal, buccal route. In a preferred embodiment, the pharmaceutical composition of the invention may be adapted for oral or intravenous administration.

The pharmaceutical composition may be in the solid or the liquid dosage form. The solid dosage form may be suitable for administration to a patient according to a continuous dosing interval of daily, weekly, three times per month, twice monthly, and monthly. The liquid dosage form may be suitable for administration to a patient according to a continuous dosing interval of daily, weekly, three times per month, twice monthly, and monthly.

The pharmaceutical composition may be administered as an aqueous solution as a bolus and/or intravenous infusion, subcutaneous injection, or orally. In a preferred embodiment, the pharmaceutical composition is administered by intravenous injection in a carrier such as distilled sterile water, saline, buffered saline, or another pharmaceutically acceptable excipient for injection.

In a preferred embodiment, the pharmaceutical composition of the invention may be adapted for oral or intravenous administration.

In a certain embodiment, the pharmaceutical composition is formulated for oral delivery, and may be in a liquid or a solid dosage form. In a certain embodiment, when in a liquid dosage form, the pharmaceutical composition may be in the form of a liquid gel capsule. The solid dosage form may be any form readily understood in the art for pharmaceutical administration.

For injectable compositions (e.g., intravenous compositions), the carrier is distilled sterile water, saline, buffered saline, or another pharmaceutically acceptable excipient for injection. Additives may include preservatives and acids or base to adjust pH, to alter solubility or uptake.

Suitable pharmaceutical compositions, e.g., compositions for oral administration, may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", $6^{th}$ Edition, Ansel et. al., (Media, Pa.: Williams and Wilkins, 1995), incorporated herein by reference, which provide information on carriers, materials (e.g., coating materials), equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides. Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions, which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The pharmaceutical composition of the invention may be designed to provide delayed, sustained, pulsatile or other modified release.

If desired, the tablets, beads, granules or particles may also contain a minor amount of nontoxic auxiliary substances such as wetting or emulsifying agents, dyes, pH buffering agents, and preservatives.

Bioadhesive formulations may also be utilized to enhance uptake or modify release. Such formulations are known in the art. See, for example, U.S. Patent Application Publication No. 2006/0045865 to Jacob, the contents of which are incorporated herein by reference.

Pharmaceutical compositions adapted for delivery via nasal or pulmonary administration may also be useful. Aerosols for the delivery of therapeutic agents to the respiratory tract have been described, for example, Adjei, A. and Garren, J. *Pharm. Res.*, 7: 565-569 (1990); and Zanen, P. and Lamm, J.-W. J. *Int. J. Pharm.*, 114: 111-115 (1995). The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung. Gonda, I. "Aerosols for delivery of therapeutic and diagnostic agents to the respiratory tract," in *Critical Reviews in Therapeutic Drug Carrier Systems*, 6:273-313 (1990). The deep lung, or alveoli, is the primary target of inhaled therapeutic aerosols for systemic drug delivery.

Drugs administered by inhalation may come as liquid aerosol formulations.

When the pharmaceutical composition is in a liquid dosage form, it may have a pH between about 6.5 and about 8.5. In certain embodiments, the pharmaceutical composition contains an acid, a base, and or a combination thereof, which is used to adjust the pH to the desired pH range. In a certain embodiment, the pH is from about 7.0 to about 8.0, and preferably from about 7.2 to about 7.6.

Any acid or base known for use in pharmaceutical compositions may be used in accordance with the invention. In a certain embodiment, the acid or base is selected from carbonate, bicarbonate, sodium hydroxide, acetic acid, sulfuric acid, hydrochloric acid, and any combination thereof. Preferably, hydrochloric acid may be used as the acid, and sodium hydroxide may be used as the base.

In an embodiment, the pharmaceutical composition may be adjusted to about 5 mg/ml to about 500 mg/ml, preferably, to about 5 mg/ml to about 250 mg/ml, more preferably, to about 5 mg/ml to about 50 mg/ml, and most preferably, to about 10 mg/ml to about 25 mg/ml of the HDAC inhibitor, and about 5 mg/ml to about 500 mg/ml, preferably, to about 5 mg/ml to about 250 mg/ml, more preferably, to about 5 mg/ml to about 50 mg/ml, and most preferably, to about 10 mg/ml to about 25 mg/ml of the IKK inhibitor.

In an embodiment, the pharmaceutical composition formulated in a liquid dosage form, preferably for intravenous administration, contains about 1 to about 75 mg/mL, preferably about 5 to about 70 mg/mL, and more preferably about 10 to about 56 mg/mL of the HDAC inhibitor, and contains about 1 to about 75 mg/mL, preferably about 5 to about 70 mg/mL, and more preferably about 10 to about 56 mg/mL of the IKK inhibitor.

In an embodiment, the pharmaceutical composition formulated in a solid dosage form, preferably for oral administration, contains about 10 to about 500 mg per dose, preferably about 50 to 200 mg per dose, and most preferably about 100 mg per dose of the HDAC inhibitor. Each dose may preferably be in the form of a capsule.

The terms used in these embodiments of the invention, such as "HDAC inhibitor," "IKK inhibitor," "therapeutically effective amount," and "solid tumor cancer," have the same meaning as they have in the embodiments described above.

III. Kit

Another embodiment of the invention is a kit comprising: a therapeutically effective amount of a histone deacetylase (HDAC) inhibitor; and a therapeutically effective amount of an IκB kinase (IKK) inhibitor.

In the kit, the HDAC inhibitor and the IKK inhibitor may be included as separate doses or together in the form of a pharmaceutical composition, as described above. In a preferred embodiment, the kit comprises an HDAC inhibitor and an IKK inhibitor formulated for oral or intravenous delivery.

When formulated as a solid dosage form for oral administration, the kit may contain about 100 mg to about 800 mg per dose, preferably about 100 mg to about 600 mg per dose, more preferably, about 200 mg to about 600 mg per dose, and most preferably about 300 mg to about 400 mg per dose, of the HDAC inhibitor, and about 100 mg to about 2000 mg per dose, preferably about 200 mg to about 1000 mg per dose, more preferably, about 200 mg to about 600 mg per dose, and most preferably about 300 mg to about 400 mg per dose, of the IKK inhibitor.

When formulated in a liquid dosage form, preferably for intravenous administration, the kit may contain about 1 to about 75 mg/mL, preferably about 5 to about 70 mg/mL, and more preferably about 10 to about 56 mg/mL of the HDAC inhibitor, and contain about 1 to about 75 mg/mL, preferably about 5 to about 70 mg/mL, and more preferably about 10 to about 56 mg/mL of the IKK inhibitor.

In another embodiment, the kit containing an HDAC inhibitor and an IKK inhibitor is useful for the treatment of solid tumor cancers. In an embodiment thereof, the kit comprises a container.

The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold an HDAC inhibitor, an IKK inhibitor, both inhibitors separately, or a pharmaceutical composition thereof which is effective for treating the solid tumor cancer and may have a sterile access port (for example, the container may be an intravenous solution bag or a vial having a stopper pierceable by a hypodermic injection needle).

The label or package insert indicates that the combination therapy is used for treating the condition of choice, such as ovarian cancer. In one embodiment, the label or package insert indicates that the combination therapy comprising an HDAC inhibitor and an IKK inhibitor can be used to treat a drug-resistant solid tumor. The label or package insert may also indicate that the combination therapy can be used to treat other diseases. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the HDAC inhibitor and IKK inhibitor. For example, the kit may comprise directions for the simultaneous, sequential or separate administration of the HDAC inhibitor and the IKK inhibitor to a subject in need thereof.

In another embodiment, the kits are suitable for the delivery of solid oral forms of an HDAC inhibitor and an IKK inhibitor, such as tablets or capsules. Such a kit preferably includes a number of unit dosages. Such kits can include a card having the dosages oriented in the order of their intended use. An example of such a kit is a "blister pack." Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise: (a) a first container with an HDAC inhibitor contained therein; and (b) a second container with an IKK inhibitor contained therein. The kit may comprise a container for containing the separate actives such as a divided bottle or a divided foil packet. However, the separate actives may also be contained within a single, undivided container. Typically, the kit comprises directions for the administration of the separate actives. The kit form is particularly advantageous when the separate components are preferably administered in different dosage forms (e.g., oral and parenteral), are administered at different dosage intervals, or when titration of the individual actives is desired by the prescribing physician.

The entire contents of all references, patent applications, and patents cited throughout this application are hereby incorporated by reference herein.

EXAMPLES

The invention will be further illustrated in the following nonlimiting Examples. These Examples are set forth to aid in the understanding of the invention but are not intended to, and should not be construed to, limit its scope in any way. The Examples do not include detailed descriptions of conventional methods that are well known to those of ordinary skill in the art.

Example 1: HDAC Inhibitors Increase IL-8 Expression in Ovarian Cancer Cells

Methods: Human ovarian cancer SKOV3 cells were obtained from the American Type Culture Collection and cultured in RPMI 1640 medium supplemented with 10% heat inactivated fetal bovine serum (FBS) and antibiotics (100 units/mL penicillin and 100 μg/mL streptomycin) at 37° C., 5% $CO_2$, humidified atmosphere. $5\times10^5$ cells/ml were seeded in 6-well plates and incubated 48 hours with 0; 1; 1.5; 2; and 5 μM vorinostat, or 0; 5; 10; 20; and 40 nM romidepsin. An equivalent volume of DMSO (final concentration 0.1% v/v) was used as a vehicle control. After 48 hours, cells were collected by centrifugation for analysis of cytokine mRNA levels of NF-kB-dependent cytokines, IL-8, TNF, and IL-6, by quantitative RT-PCR, and cell culture supernatants were collected for analysis of released IL-8, TNF and IL-6 cytokine release by ELISA. Total RNA was isolated by using RNeasy mini-kit (Qiagen) (See, e.g., Singha, B. et al., "Quantitative analysis of bortezomib-induced IL-8 gene expression in ovarian cancer cells," Methods Mol. Biol., Vol. 1172, pp. 295-304 (2014)). The iScript one-step RT-PCR kit with SYBR Green (BioRad) was used as a supermix and 20 ng of RNA was used as template on a Bio-Rad MyIQ Single Color Real-Time PCR Detection System (BioRad). The primers used for quantification of IL-8, TNF, IL-6, and control actin mRNA were purchased from SA Biosciences. The amount of IL-8 released into the cell culture media was quantified using human IL-8 ELISA kit (R&D). The results are presented as means+/−SE. Data were analyzed by using InStat software package (GraphPAD). Statistical significance was evaluated by using ANOVA, and $p<0.05$ was considered significant.

Figure 1A:
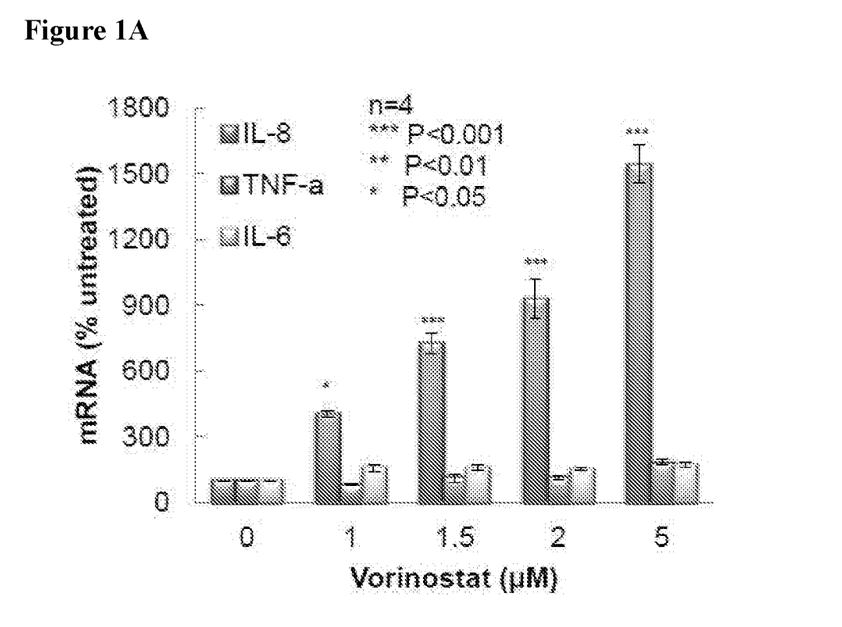
FIGS. 1A and 1B are graphs showing IL-8 mRNA levels and IL-8 cytokine release concentrations, respectively, in SKOV3 ovarian cancer cells after treatment with vorinostat as described in Example 1.
Figure 1B:
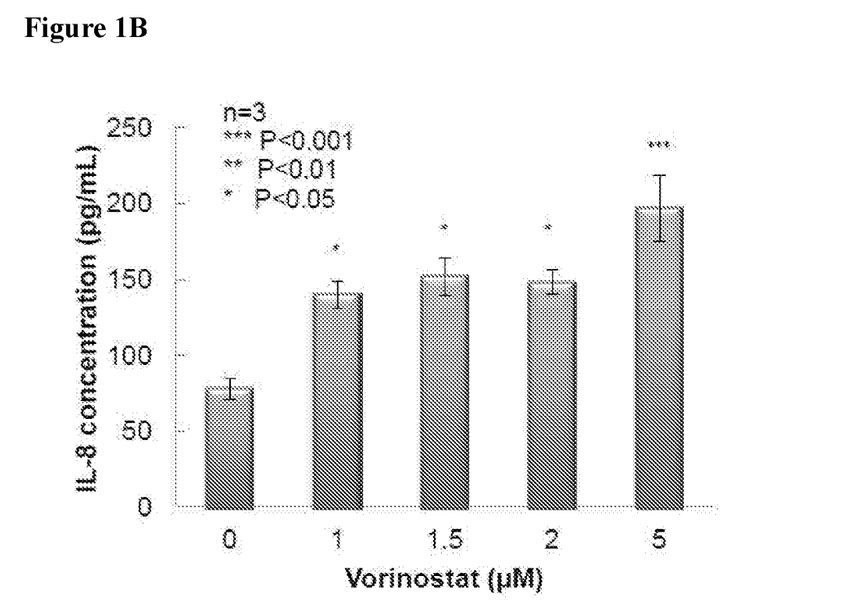
Figure 2A:
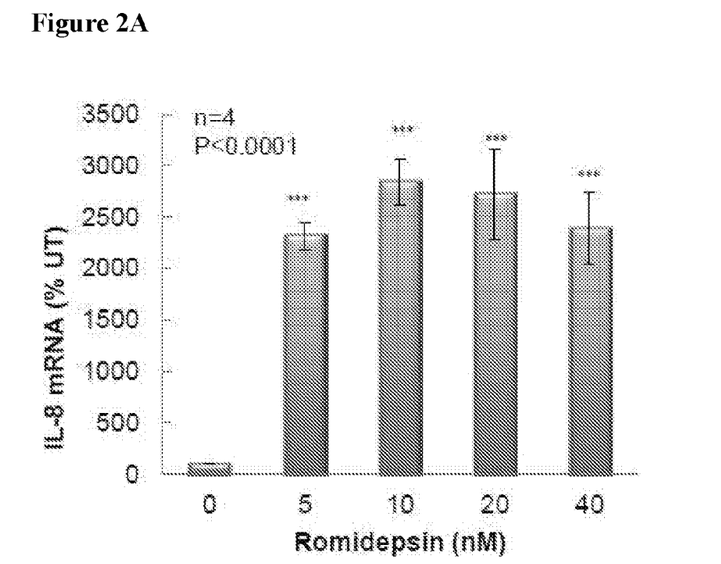
FIGS. 2A and 2B are graphs showing IL-8 mRNA levels and IL-8 cytokine release concentrations, respectively, in SKOV3 ovarian cancer cells after treatment with romidepsin as described in Example 1.
Figure 2B:
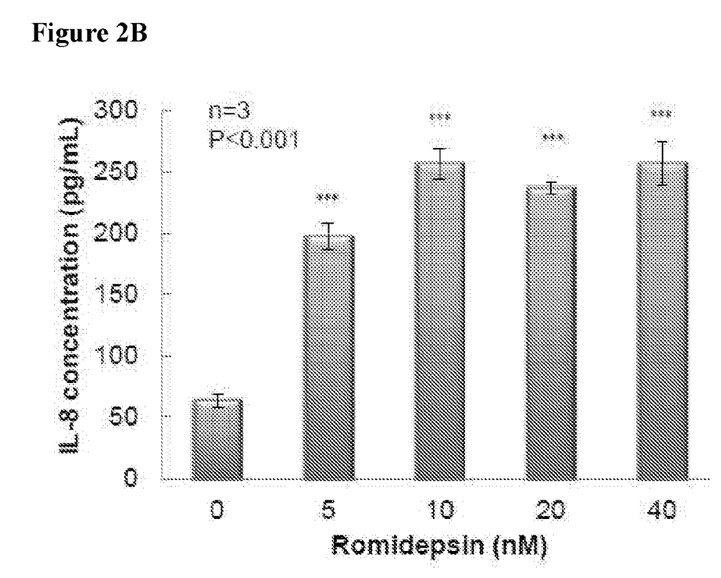

Results: The graphical results shown in FIGS. 1A-B and 2A-B demonstrate that HDAC inhibitors, vorinostat and romidepsin, significantly increase the IL-8 expression in ovarian cancer cells. Specifically, the results show that HDAC inhibitors significantly increase the IL-8 mRNA levels (FIGS. 1A and 2A) and IL-8 cytokine release (FIGS. 1B and 2B) in ovarian cancer cells. Vorinostat at 1.5 μM concentration, which approximately corresponds to the clinically used concentration, increases the IL-8 mRNA expression by about 7-fold (FIG. 1A), and increases IL-8 cytokine release by about 2-fold (FIG. 1B). Romidepsin at 10 nM concentration, which approximately corresponds to the clinically used romidepsin concentration, increases the IL-8 mRNA expression by about 28-fold (FIG. 2A) and increases IL-8 cytokine release by about 4-fold (FIG. 2B). Since IL-8 promotes survival and proliferation of ovarian cancer cells, the HDAC inhibition-induced IL-8 release demonstrated by the results of this study may provide an explanation for the decreased effectiveness of HDAC inhibitors when used as single agents in ovarian cancer treatment.

Example 2: HDAC Inhibitors Increase IL-8 Expression in Cervical Cancer Cells

Methods: Human cervical cancer HeLa cells were obtained from American Type Culture Collection and cultured in Eagle's Minimum Essential Medium supplemented with 10% FBS and antibiotics (100 units/mL penicillin and 100 μg/mL streptomycin) at 37° C., 5% $CO_2$, humidified atmosphere. $5\times10^5$ cells/ml were seeded in 6-well plates and incubated 48 hours with 0; 1; 1.5; 2; and 5 μM vorinostat, or 0; 5; 10; 20; and 40 nM romidepsin. An equivalent volume of DMSO (final concentration 0.1% v/v) was used as a vehicle control. After 48 hours, cells were collected by centrifugation for analysis of cytokine mRNA levels of IL-8, TNF, and IL-6 by quantitative RT-PCR. Total RNA was isolated by using RNeasy mini-kit (Qiagen), and the real time RT-PCR was performed as described in Example 1. The results are presented as means+/−SE. Data were analyzed by using InStat software package (GraphPAD). Statistical significance was evaluated by using ANOVA, and $p<0.05$ was considered significant.

Figure 3A:
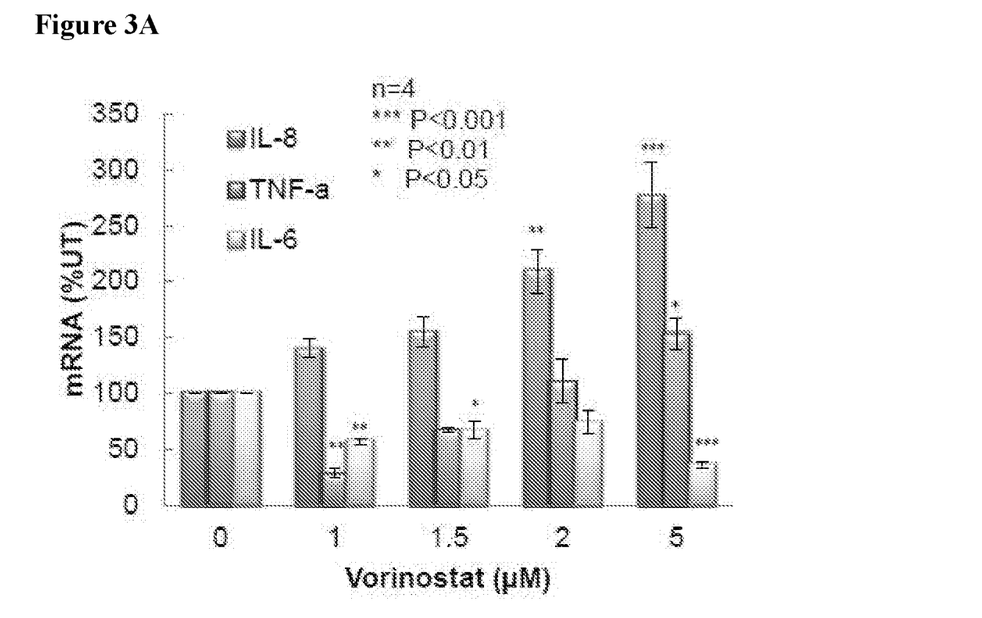
FIGS. 3A and 3B are graphs showing IL-8 mRNA levels in HeLa cervical cancer cells after treatment with vorinostat and romidepsin, respectively, as described in Example 2.
Figure 3B:
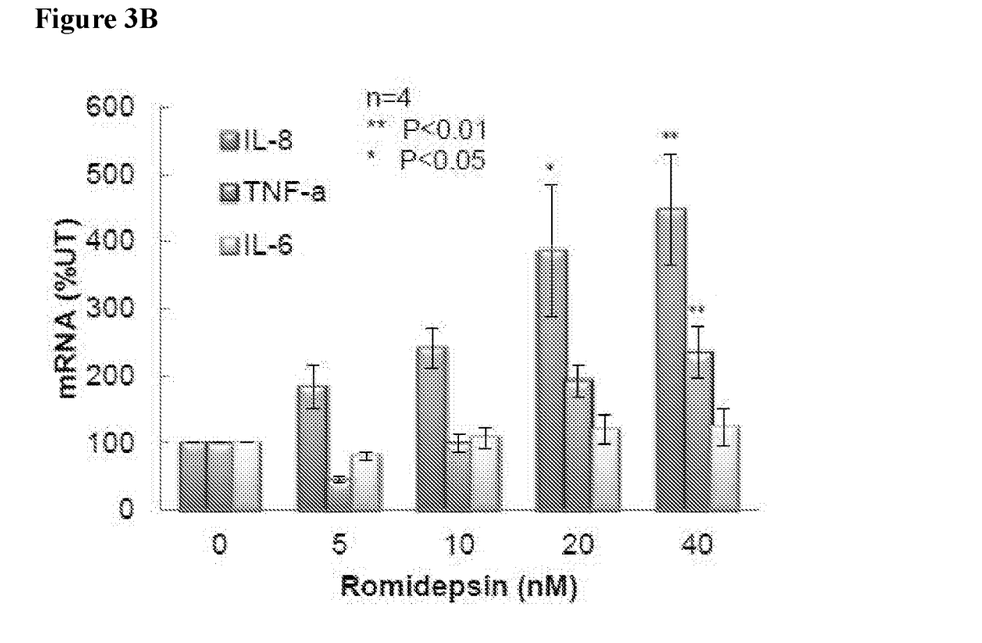

Results: The graphical results shown in FIGS. 3A-B demonstrate that HDAC inhibitors, vorinostat and romidepsin, significantly increase IL-8 mRNA expression in cervical cancer cells. The HDAC inhibition-induced IL-8 expression demonstrated by the results of this study may provide an explanation for the decreased effectiveness of HDAC inhibitors when used as single agents in the treatment of solid tumors.

Figure 4A:
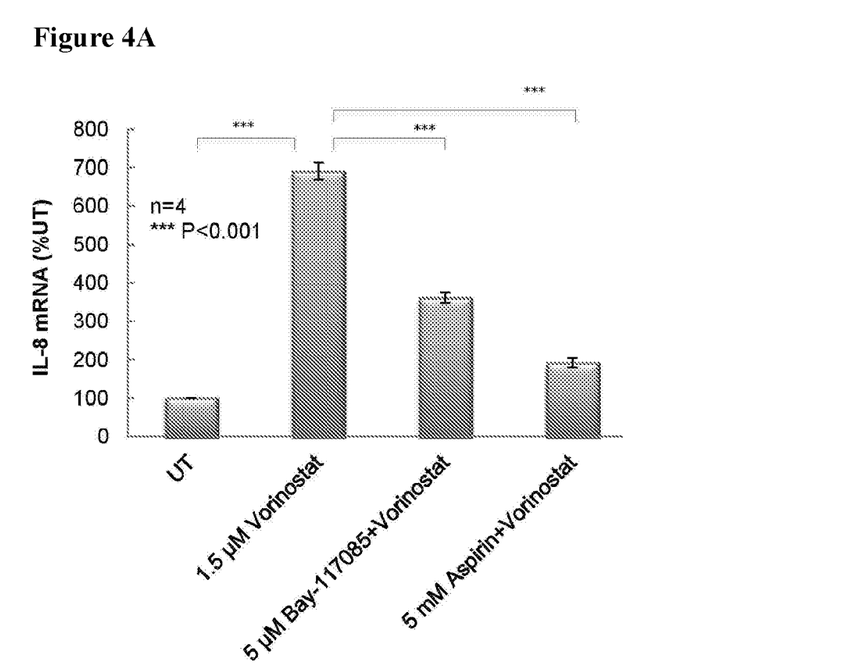
FIGS. 4A and 4B are graphs showing IL-8 mRNA levels and IL-8 cytokine release concentrations, respectively, in SKOV3 ovarian cancer cells after treatment with vorinostat and IKK inhibitors as described in Example 3.
Figure 4B:
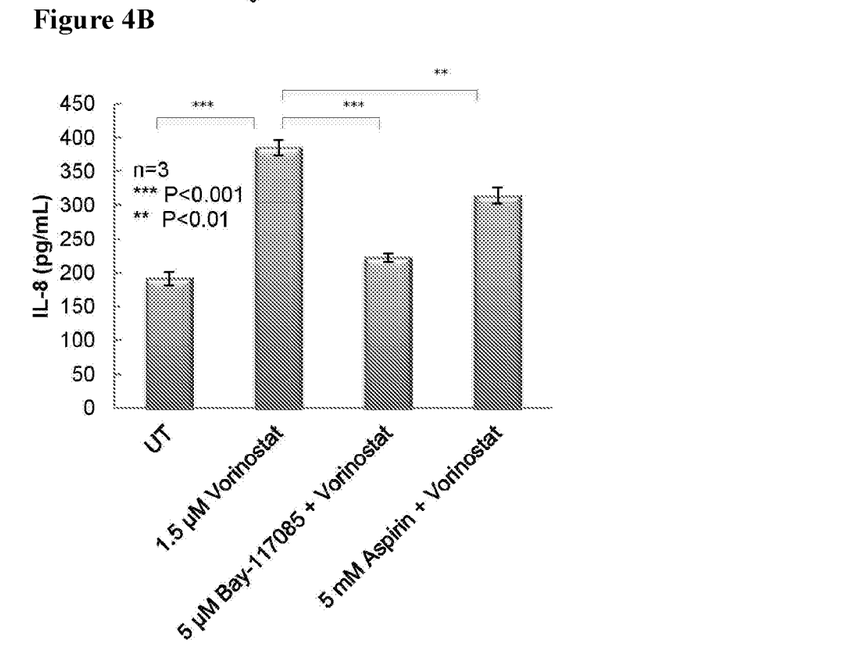
Figure 5A:
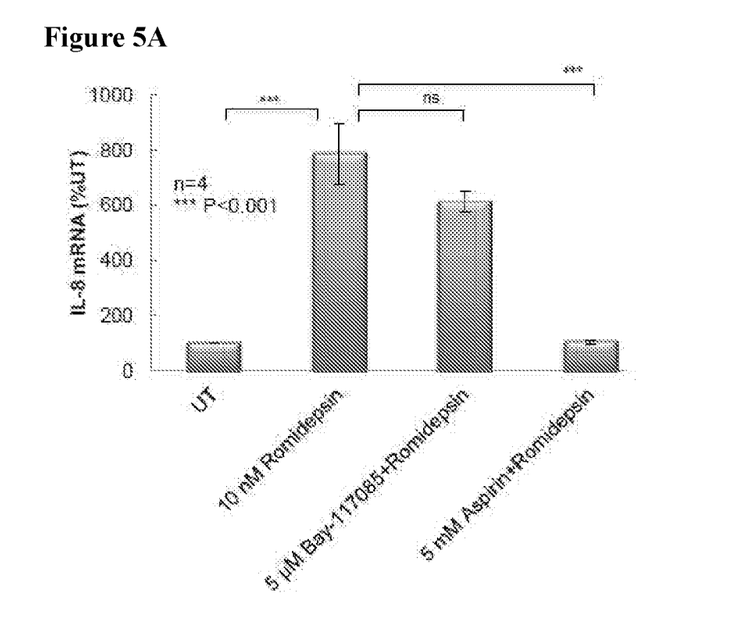
FIGS. 5A and 5B are graphs showing IL-8 mRNA levels and IL-8 cytokine release concentrations, respectively, in SKOV3 ovarian cancer cells after treatment with romidepsin and IKK inhibitors as described in Example 3.
Figure 5B:
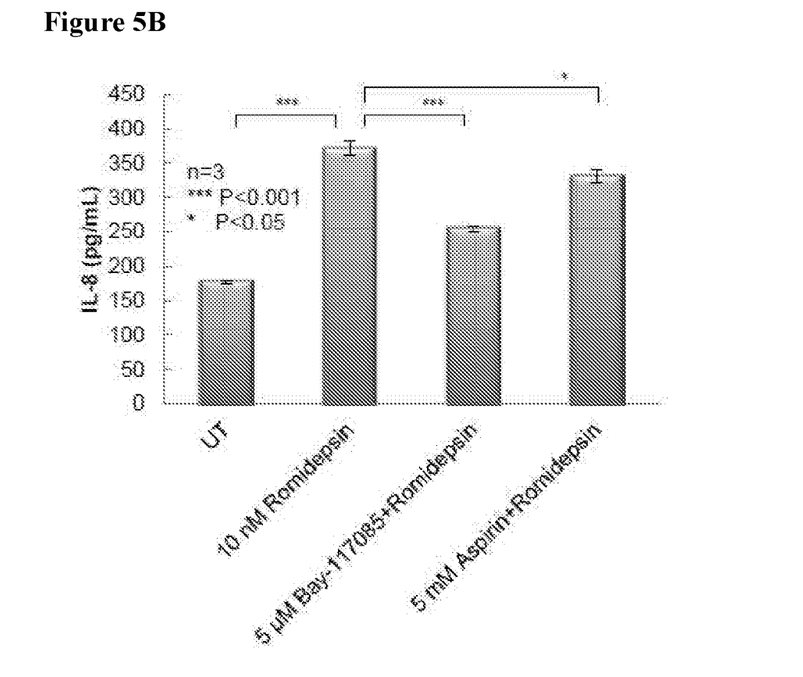

Example 3: IKK Inhibitors Suppress the HDAC Inhibition-Induced IL-8 Expression in Ovarian Cancer Cells Methods: Human ovarian cancer SKOV3 cells ($5 \times 10^5$ cells/ml) were incubated 12 hours with an IKK inhibitor, Bay-117085 (5 µM) or aspirin (5 mM), followed by 48-hour incubation with an HDAC inhibitor, 1.5 vorinostat (see FIG. 4A-B) or 10 nM romidepsin (see FIG. 5A-B). These concentrations for vorinostat and romidepsin approximately correspond to the clinically used amounts. After the 48-hour incubation with the HDAC inhibitor, cells were collected for IL-8 mRNA levels and analyzed by RT-PCR, and cell culture supernatants were collected for analysis of IL-8 cytokine release by ELISA. Analysis of IL-8 mRNA levels by quantitative RT-PCR and IL-8 cytokine release by ELISA were performed as described in Example 1. The results are presented as means+/−SE. Data were analyzed by using InStat software package (GraphPAD). Statistical significance was evaluated by using ANOVA, and $p<0.05$ was considered significant.

Results: As observed in Example 1 and shown in the bar graphs of FIGS. 4A-B and 5A-B (second bar in from the left in each graph), HDAC inhibitors alone significantly increase IL-8 mRNA expression (FIGS. 4A and 5A) and cytokine release (FIGS. 4B and 5B) in ovarian cancer cells. From the results of this study, it was shown that introduction of an IKK inhibitor, Bay-117085 or aspirin, significantly decreases (or suppresses) the IL-8 mRNA expression and IL-8 release induced by the HDAC inhibitor in ovarian cancer cells. The in vitro data demonstrates that the HDAC inhibitor-induced IL-8 production is mediated by IKK. Therefore, including an IKK inhibitor in a treatment regimen may increase effectiveness of HDAC inhibitors in the suppression of tumor growth in vivo.

Figure 6:
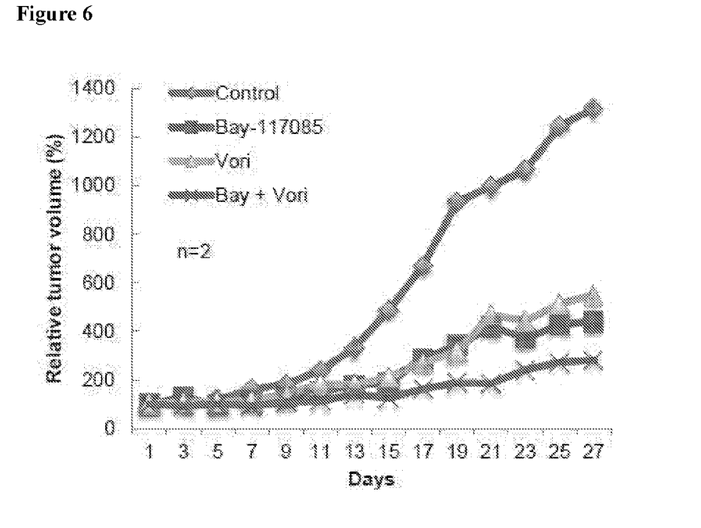
FIG. 6 is a graph showing relative tumor volume over time in nude mice implanted with ovarian cancer SKOV3 xenografts and treated with either a control solution, vorinostat, Bay-117085, or a combination therapy of Bay-117085 and vorinostat. The study is described in Example 4.
Figure 7A:
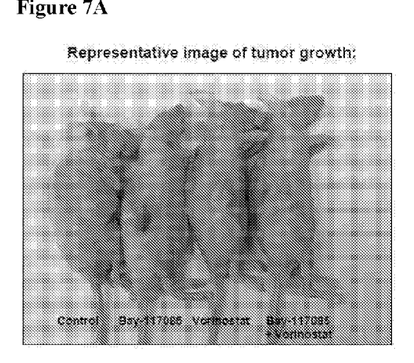
FIG. 7A is a postmortem image of nude mice implanted with ovarian cancer xenografts and FIG. 7B is an image showing the excised tumors, described in Example 4.
Figure 7B:
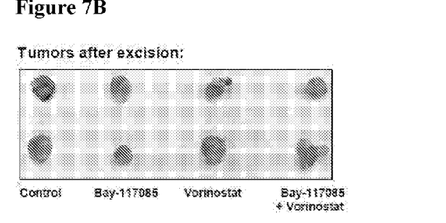

Example 4: Combination of HDAC Inhibitor and IKK Inhibitor Enhances the HDAC Inhibitor Effectiveness in Reducing Solid Tumor Growth in Vivo Methods: Five-week-old female athymic nude mice (Taconic Farms) were used for tumor xenograft experiments. Mice were maintained on an alternating 12 hours light/dark cycle with ad libitum water and rodent chow. Mice were subcutaneously (s.c.) injected in the right flanks with $5 \times 10^6$ of SKOV3 cells in 300 µl of serum free RPMI media. Dimensions (length and width) of the solid tumors were recorded using calipers and the tumor volumes were calculated using the formula: volume=length×width$^2$×0.5. Once the average tumor size reached about 70 mm$^3$, mice were randomly divided into four treatment groups. The control group received vehicle solution, phosphate buffered saline, injected intra-peritoneally (i.p) every other day for 4 consecutive weeks. The IKK inhibitor group received Bay-117085 (5 mg/kg) injected i.p every other day. The HDAC inhibitor group received vorinostat (50 mg/kg) injected i.p every other day. The combination therapy group received Bay-117085 and vorinostat injected i.p every other day for 4 consecutive weeks. Mice were weighed, and tumor volume was monitored by caliper measurement every other day. Tumor volumes were calculated using the following formula: Volume=length×width$^2$×0.5. Relative tumor volumes were calculated every other day by dividing volume at the indicated day by volume at the starting day of the treatment. A graph depicting the results is shown in FIG. 6. After 28 days of the treatment, mice were euthanized and arranged for a representative image showing the tumor growth (FIG. 7A). FIG. 7B shows excised tumors in the individual treatment groups.

Results: Results illustrated in FIG. 6 show that, when compared to the control untreated group or the group treated with vorinostat alone, mice in the Bay-117085/vorinostat combination therapy group exhibited the slowest tumor growth. After four weeks of therapy, the tumor growth in the combination therapy group was about 80% slower compared to the control untreated group. Importantly, after four weeks of therapy, the tumor growth in the combination therapy group was about 50% slower compared to the group treated with vorinostat alone (FIG. 6). Therefore, a combination therapy of the HDAC inhibitor vorinostat and the IKK inhibitor Bay-117085 enhances vorinostat effectiveness in reducing tumor growth in vivo, in nude mice implanted with ovarian cancer xenografts.

Thus, this study demonstrates that incorporating an IKK inhibitor in a combination therapy may increase effectiveness of an HDAC inhibitor in the treatment of solid tumors.

What is claimed is:

1. A method for treating a solid tumor cancer comprising administering to a subject in need thereof a therapeutically effective amount of a histone deacetylase (HDAC) inhibitor and a therapeutically effective amount of an IκB kinase (IKK) inhibitor.

2. The method of claim 1, wherein the HDAC inhibitor is administered in combination, sequentially, or concomitantly with the IKK inhibitor.

3. The method of claim 2, wherein the HDAC inhibitor and the IKK inhibitor are administered concomitantly.

4. The method of claim 2, wherein the HDAC inhibitor and the IKK inhibitor are administered sequentially.

5. The method of claim 1, wherein the HDAC inhibitor and the IKK inhibitor are administered intravenously or orally.

6. The method of claim 5, wherein the HDAC inhibitor and the IKK inhibitor are administered intravenously.

7. The method of claim 5, wherein the HDAC inhibitor and the IKK inhibitor are administered orally.

8. The method of claim 5, wherein one of the HDAC inhibitor or the IKK inhibitor is administered intravenously and the other of the HDAC inhibitor or the IKK inhibitor is administered orally.

9. The method of claim 1, wherein the solid tumor is drug-resistant.

10. The method of claim 1, wherein the solid tumor is selected from the group consisting of a bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and any combination thereof.

11. The method of claim 10, wherein the solid tumor is ovarian cancer.

12. The method of claim 10, wherein the solid tumor is breast cancer.

13. The method of claim 12, wherein the solid tumor is triple negative breast cancer.

14. The method of claim 10, wherein the solid tumor is prostate cancer.

15. The method of claim 14, wherein the solid tumor is androgen-independent prostate cancer.

16. The method of claim 1, wherein the subject is a mammal.

17. The method of claim 16, wherein the subject is a human.

* * * * *